United States Patent
Otsubo et al.

(10) Patent No.: US 8,961,488 B2
(45) Date of Patent: Feb. 24, 2015

(54) WEARING ARTICLE

(75) Inventors: Toshifumi Otsubo, Kagawa (JP);
Tatsuya Hashimoto, Kagawa (JP);
Mariko Yamashita, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 687 days.

(21) Appl. No.: 13/262,309

(22) PCT Filed: Mar. 31, 2010

(86) PCT No.: PCT/JP2010/002384
§ 371 (c)(1),
(2), (4) Date: Sep. 30, 2011

(87) PCT Pub. No.: WO2010/113510
PCT Pub. Date: Oct. 7, 2010

(65) Prior Publication Data
US 2012/0022488 A1 Jan. 26, 2012

(30) Foreign Application Priority Data

Mar. 31, 2009 (JP) .................................. 2009-087620

(51) Int. Cl.
*A61F 13/15* (2006.01)

(52) U.S. Cl.
USPC ............... 604/385.25; 604/385.201; 604/373; 604/385.29; 604/385.24; 604/385.27; 604/385.26

(58) Field of Classification Search
USPC .................... 604/385.01, 378, 379, 380, 373, 604/385.24, 385.29, 385.28, 385.201, 604/385.25, 385.26, 385.27
See application file for complete search history.

(56) References Cited

U.S. PATENT DOCUMENTS

| 4,747,846 | A | | 5/1988 | Boland et al. |
| 6,017,406 | A | * | 1/2000 | Vogt .............................. 156/73.1 |
| 6,140,551 | A | | 10/2000 | Niemeyer et al. |
| 6,613,033 | B1 | * | 9/2003 | Popp et al. ............... 604/385.25 |
| 2007/0250983 | A1 | * | 11/2007 | Thompson et al. .................. 2/69 |
| 2008/0125740 | A1 | * | 5/2008 | Wakasugi et al. ........ 604/385.29 |

FOREIGN PATENT DOCUMENTS

| EP | 0 650 714 A1 | 5/1995 |
| JP | 62-21802 A | 1/1987 |
| JP | 1-503473 A | 11/1989 |
| JP | 2000-107227 A | 4/2000 |
| JP | 2003-135515 A | 5/2003 |
| JP | 2003-220092 A | 8/2003 |
| JP | 2004-298467 A | 10/2004 |
| JP | 2007-097979 A | 4/2007 |
| JP | 2008-173285 A | 7/2008 |
| WO | 2008-066006 A1 | 6/2008 |

OTHER PUBLICATIONS

International Search Report for PCT/JP2010/002384 mailed Jul. 6, 2010.
European Search Report mailed Dec. 2, 2014 in corresponding European Application No. 10758289.2.

* cited by examiner

*Primary Examiner* — Jacqueline F. Stephens
(74) *Attorney, Agent, or Firm* — Lowe Hauptman & Ham LLP

(57) ABSTRACT

A wearing article has a chassis and leg elastic members of a flat band shape that are attached to the chassis along leg side edges thereof. The chassis has regions each of which overlaps one of the leg elastic members and includes at least one series of depressions extending along the respective leg side edge.

9 Claims, 8 Drawing Sheets

WEARING ARTICLE

RELATED APPLICATIONS

The present application is a National Phase of International Application Number PCT/JP2010/002384, filed Mar. 31, 2010 and claims priority from, Japanese Application Number 2009-087620, filed Mar. 31, 2009.

TECHNICAL FIELD

The present disclosure relates to wearing articles and, more particularly, to absorbent articles such as disposable diapers, toilet-training pants or incontinent briefs.

BACKGROUND

Disposable diapers are known, for example, from JP 62-21802 A, to comprise a chassis having opposite waist side edges defining a waist-opening and leg side edges defining a pair of leg-openings, and relatively wide belt-like leg elastic members provided along the respective leg side edges. In such a diaper, an elastically stretchable and contractible urethane foam (spandex) is used as the leg elastic members. By use of the leg elastic members having a relatively large width-dimension, regions to be elasticized along the respective leg side edges can be enlarged and contractile force thereof can be prevented from being locally concentrated, thereby reducing the likelihood of occurrences of skin trouble on the wearer's skin.

When such a diaper is put on a wearer's body, the leg side edges might be difficult to be folded along the wearer's inguinal regions corresponding to the respective leg-openings because of a total thickness as well as a total stiffness of the chassis and the belt-like elastic members laminated one another in those regions. In such a case, undesirable gaps might be left between the leg side edges and the inguinal regions through which body waste may leak out from the diaper. In addition, the leg side edges might irritate the wearer's inguinal regions and cause discomfort to the wearer.

There is a need to provide a wearing article in which the leg side edges of the wearing article can be smoothly deformed along the wearer's inguinal regions to prevent body waste from leaking beyond the leg side edges without, at the same time, causing discomfort to the wearer.

CITATION LIST

Patent Literature

[PTL 1]
Japanese Patent Application Laid-Open Publication No. 62-21802A

SUMMARY

One or more embodiment of the present invention relates to a wearing article comprising a chassis including a longitudinal direction, a transverse direction, a body-facing side, a garment-facing side opposite to the body-facing side, a front waist region, a rear waist region, a crotch region extending between the front and rear waist regions and leg side edges.

In this article, leg elastic members of an elastic fibrous non-woven fabric formed into a flat band shape are attached to the chassis along the leg side edges. The chassis has regions each overlapping one of the leg elastic members and comprising at least one series of depressions extending along the respective leg side edge.

One or more further embodiment of the present invention relates to a wearing article comprising a chassis including a longitudinal direction, a transverse direction, a body-facing side, a garment-facing side opposite to the body-facing side, a front waist region, a rear waist region, a crotch region extending between the front and rear waist regions and leg side edges.

In this article, leg elastic members of a flat band shape are attached to the chassis along the leg side edges. The chassis has, along at least one of the leg elastic members, at least one folding guide line about which the chassis and the respective leg elastic member are foldable to thereby, conform in shape to a wearer's body when the diaper is being worn by the wearer.

DETAILED DESCRIPTION

Details of wearing articles according to exemplary embodiments of the present invention will be more fully understood from the description given hereunder with reference to the accompanying drawings.

Figure 1:
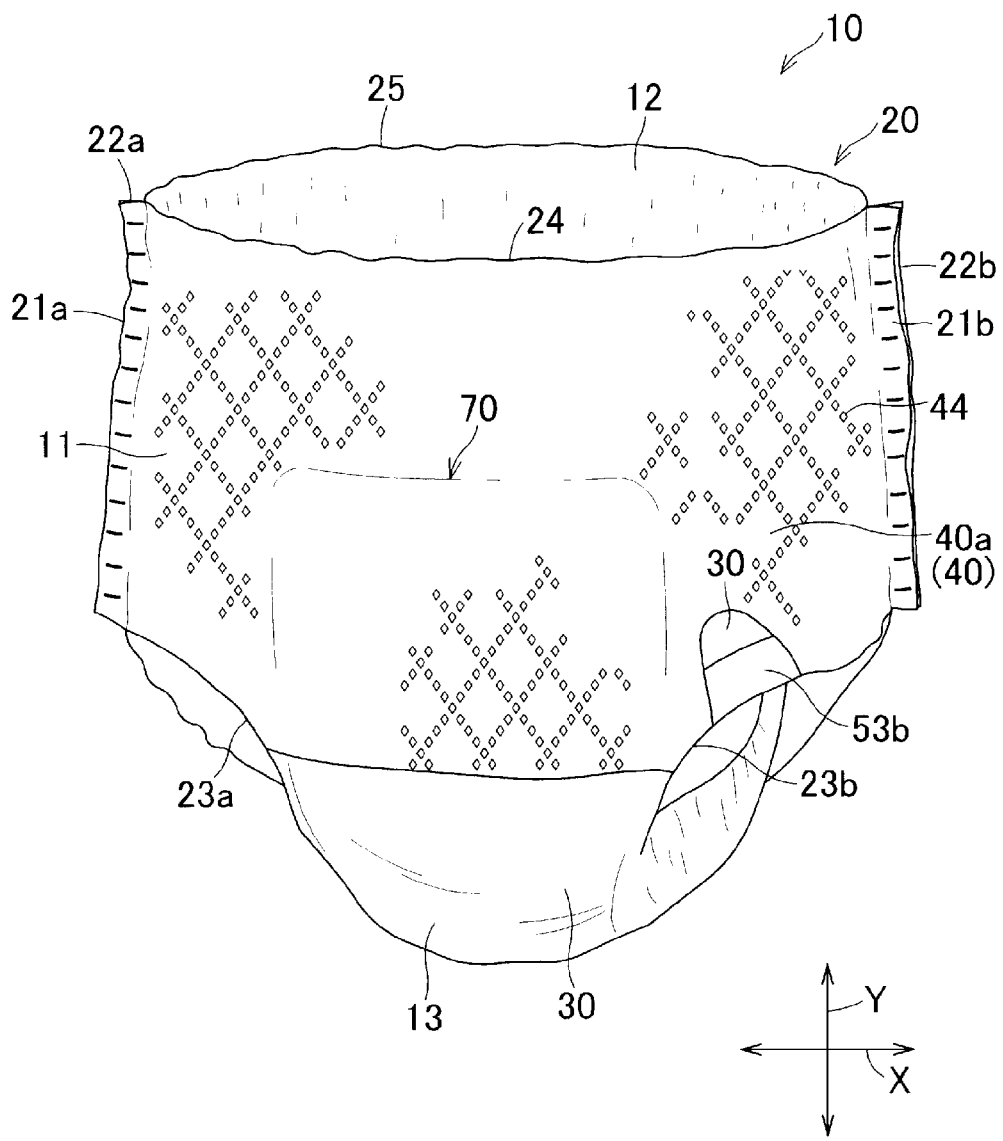
FIG. 1 is a partially cutaway perspective view of a disposable diaper in accordance with one or more embodiments.
Figure 2:
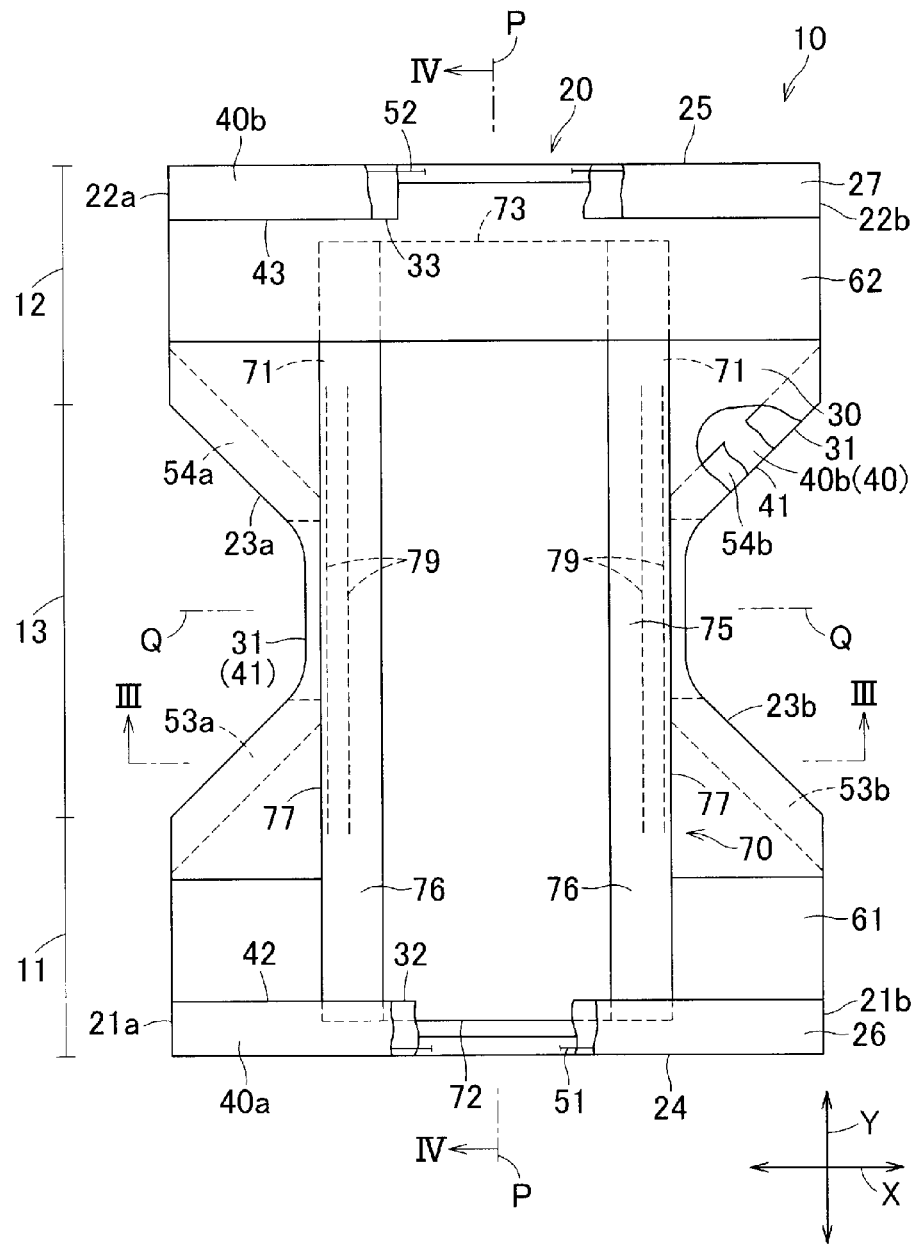
FIG. 2 is a partially cutaway plan view as viewed from the body-facing side, and showing the diaper of FIG. 1 in a flatly developed state in which the elastic elements of the diaper are in a stretched state.
Figure 3:
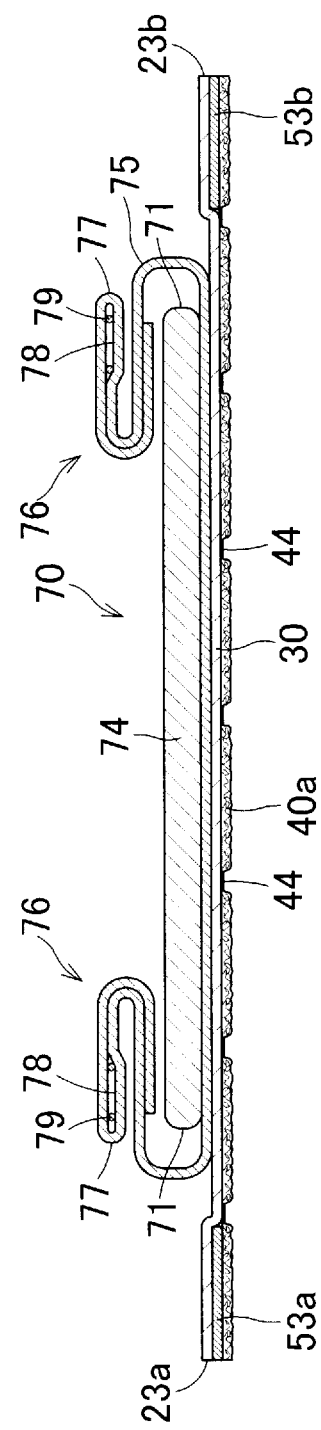
FIG. 3 is sectional view taken along the line in FIG. 2.
Figure 4:
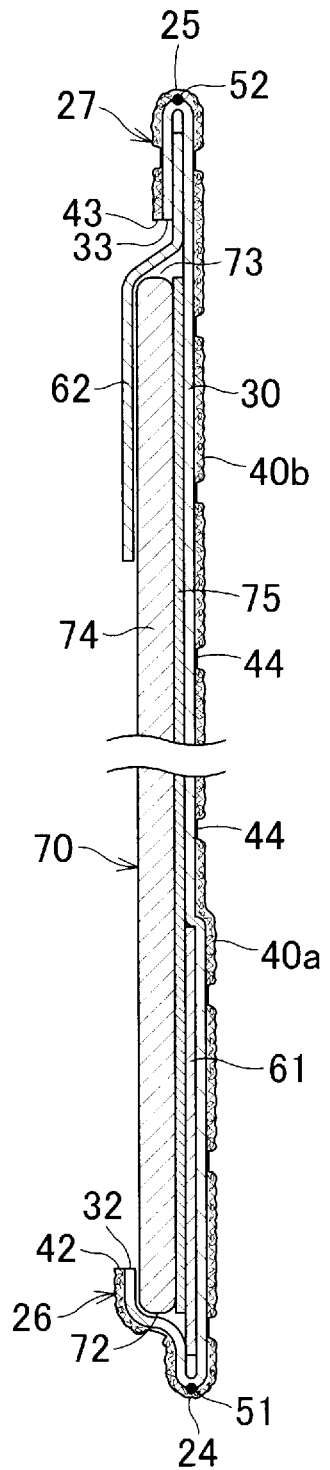
FIG. 4 is a sectional view taken along the line IV-IV in FIG. 2.
Figure 5:
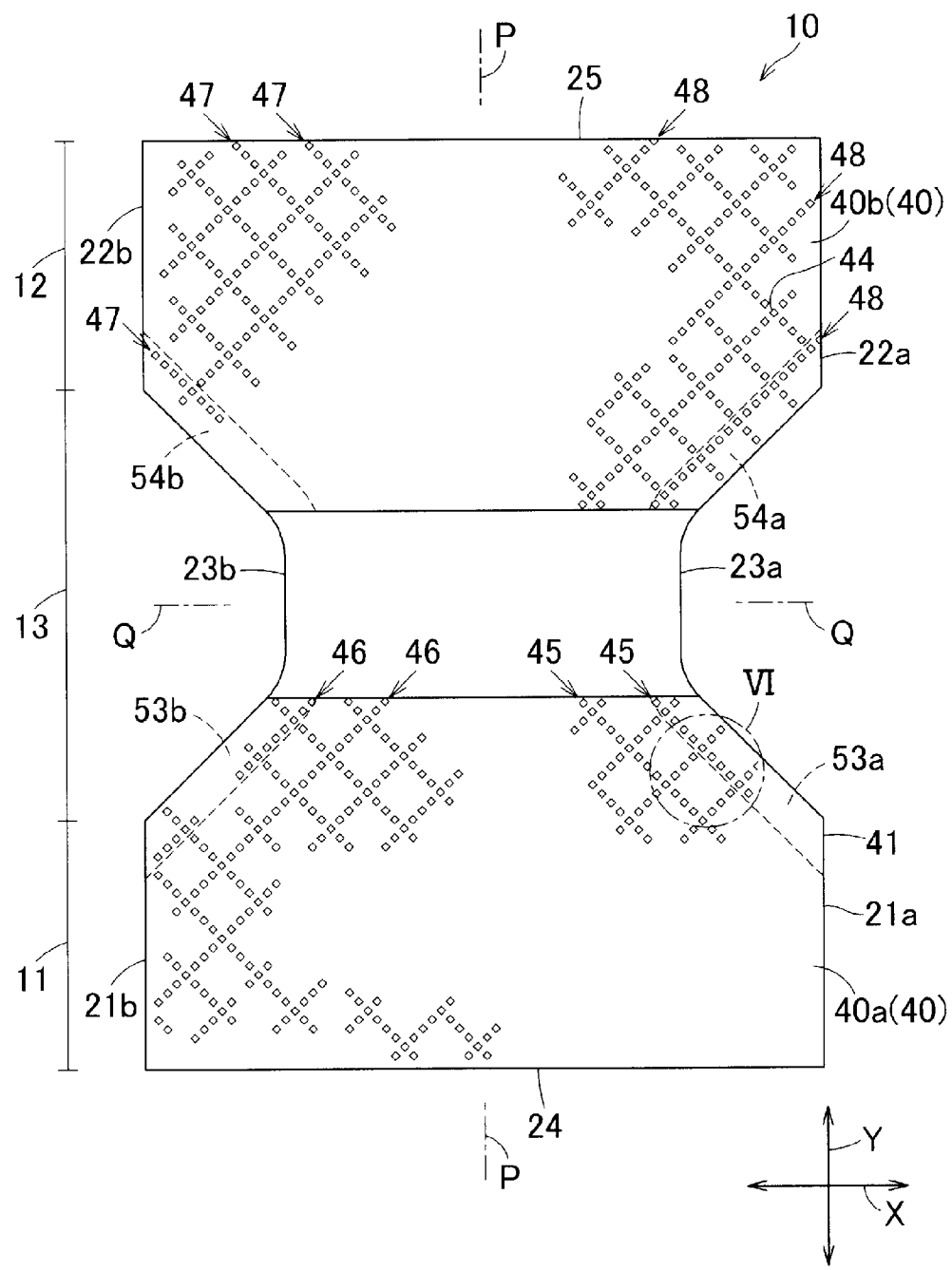
FIG. 5 is a plan view similar to FIG. 2, but viewed from the garment-facing side.
Figure 6A:
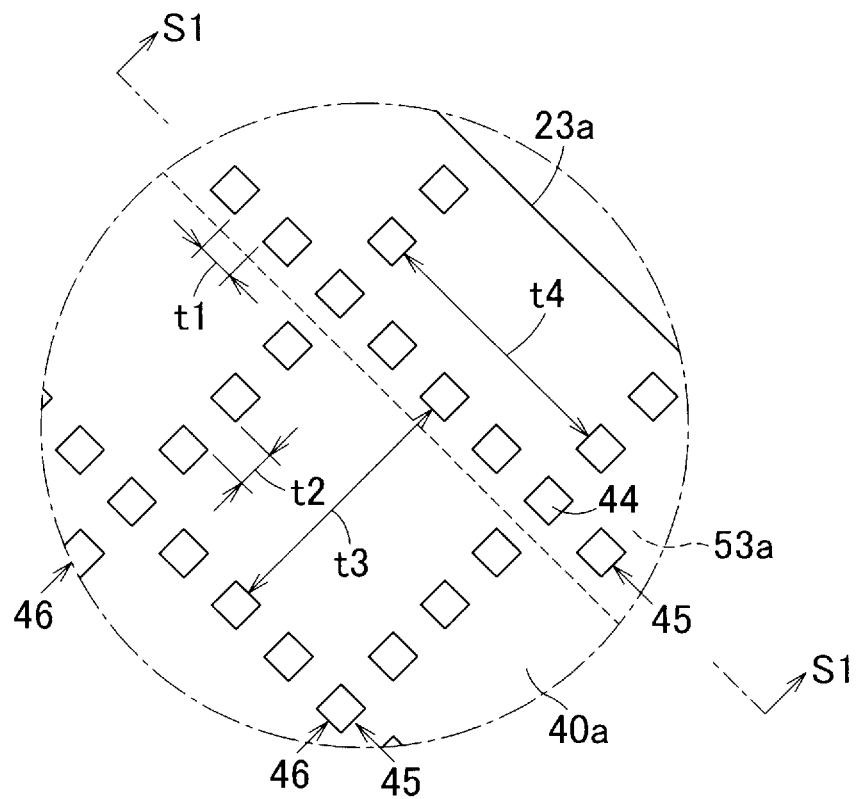
FIG. 6A is an enlarged view of a part of FIG. 5.
Figure 6B:
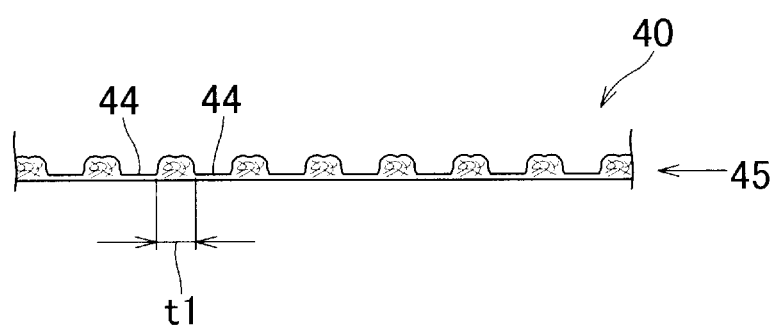
FIG. 6B is a sectional view of the outer sheet taken along the line S1-S1 in FIG. 6A.
Figure 7A:
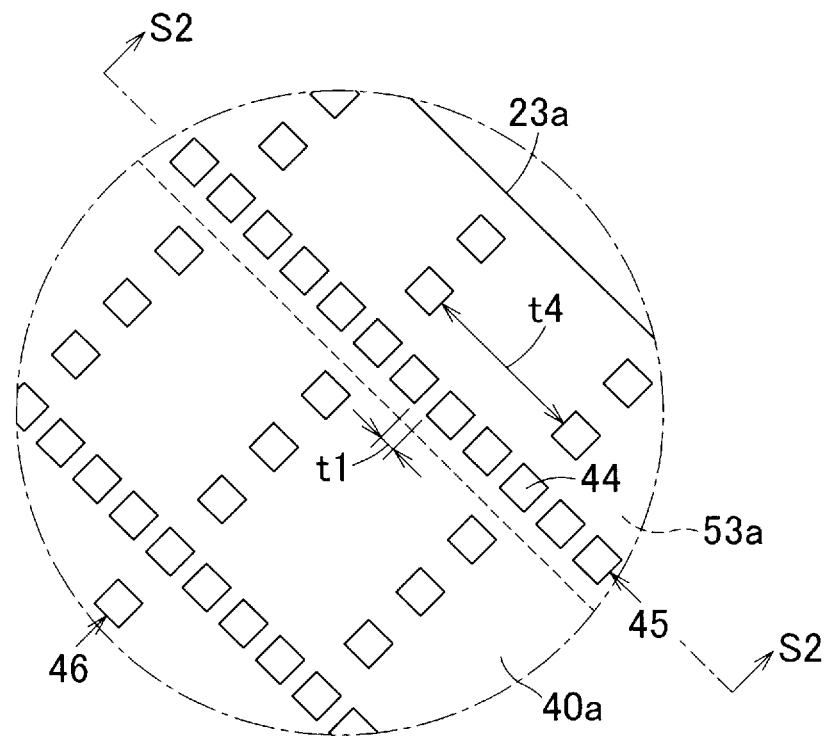
FIG. 7A is an enlarged view of substantially the same part illustrated in FIG. 6A under the contractile force of a leg elastic member.
Figure 7B:
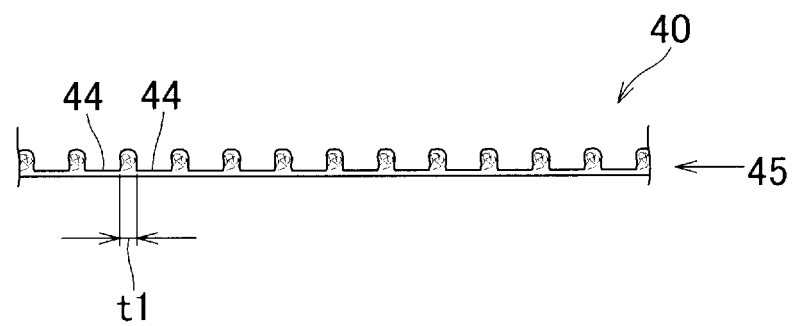
FIG. 7B is a sectional view of the outer sheet taken along the line S2-S2 in FIG. 7A.
Figure 8:
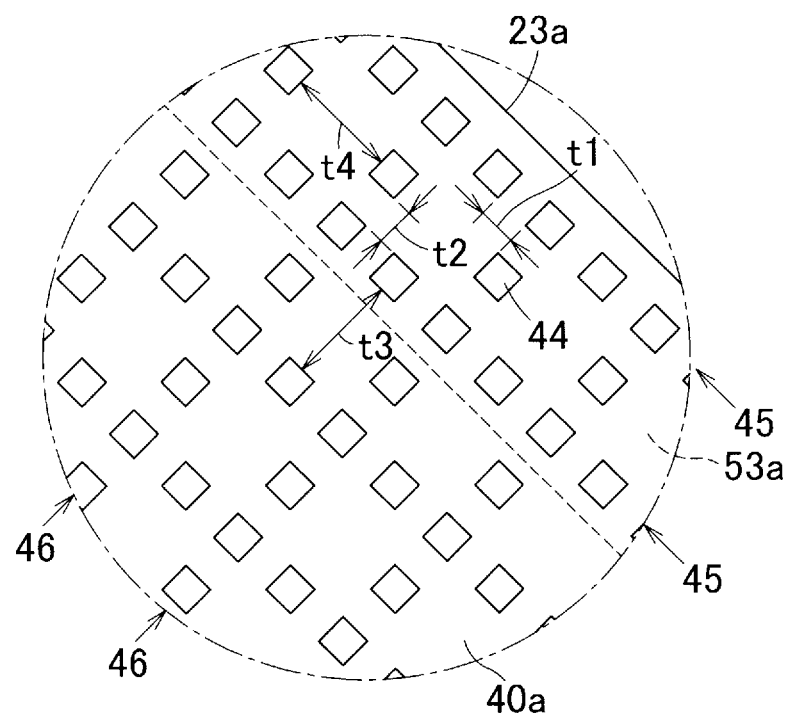
FIG. 8 is an enlarged view similar to FIG. 6A, illustrating one or more further embodiments.

FIGS. 1 through 7B are various views that illustrate a disposable diaper 10 in accordance with one or more embodiments. FIG. 8 is a view that illustrates one or more further embodiments. It should be noted that FIGS. 2-6B and 8 show the respective diapers in a state when all elastic members of the diapers are assumed to have no elasticity. FIGS. 1, 7A and 7B show the respective diapers in a state where when all elastic members of the diapers are allowed to contract and exhibit their elasticity.

The diaper 10 comprises a chassis 20 having a longitudinal direction Y, a transverse direction X, a body-facing side, a garment-facing side opposite to the body-facing side, a front waist region 11, a rear waist region 12 and a crotch region 13 extending between the front and rear waist regions 11, 12. The diaper 10 has the imaginary longitudinal center line P-P bisecting a dimension of the diaper 10 in the transverse direction X, and the imaginary transverse center line Q-Q bisecting a dimension of the diaper 10 in the longitudinal direction Y, wherein the diaper 10 is symmetrically formed about the imaginary longitudinal center line P-P.

The chassis 20 comprises inner and outer sheets 30, 40 and opposite side edges of the chassis are defined by respective pairs of opposite side edges 31, 31 and 41, 41 of the inner and outer sheets 30, 40 extending in the longitudinal direction Y. The outer sheet 40 comprises a front outer sheet section 40a lying on the front waist region 11 and a rear outer sheet section 40b lying on the rear waist region 12. These sheet sections 40a, 40b are spaced from each other in the longitudinal direction Y in the vicinity of the imaginary transverse center line Q-Q. The opposite side edges of the chassis comprise front and rear opposite waist side edges 21a, 21b, 22a, 22b lying in the front and rear waist regions 11, 12, respectively, and opposite leg side edges 23a, 23b lying in the crotch region 13. The front opposite waist side edges 21a, 21b are joined to the rear opposite waist side edges 22a, 22b and thereupon the leg-openings are defined the opposite leg side edges 23a, 23b. Front and rear ends 32, 33, 42, 43 of the inner and outer sheets 30, 40 extending in the transverse direction X are folded back toward the imaginary transverse center line Q-Q along folding lines 24, 25, respectively, with the inner sheet 30 inside to form front and rear sleeves 26, 27. The folding lines 24, 25 define the front and rear ends of the chassis and cooperate with each other to define the waist-opening.

Within the front and rear sleeves 26, 27, the front and rear waist elastic members 51, 52 extend in the transverse direction X and are attached to the chassis along the folding lines 24, 25, respectively. Specifically, the front and rear waist elastic members 51, 52 in the form of, for example, rubber strings are bonded under tension in the transverse direction X to the inner sheet 30 defining inner walls of the respective sleeves 26, 27 by adhesive (not shown). Front and rear waist sheets 61, 62 extend from the front and rear sleeves 26, 27 toward the imaginary transverse center line Q-Q. The front and rear waist sheets 61, 62 are formed of an elasticized fibrous non-woven fabric contractible at least in the transverse direction X. The front and rear waist sheets 61, 62 are attached to the chassis 20 in a stretched state in the transverse direction X to elasticize the front and rear waist regions 11, 12 so as to be elastically contractible in the transverse direction. In the particularly illustrated embodiment, the front and rear waist sheets 61, 62 serve to put the front and rear waist regions 11, 12 in close contact with the wearer's front and rear waist regions. In addition, the front and rear waist elastic members 51, 52 assure that the waist-opening is kept in close contact with the wearer's body to prevent body waste such as urine from leaking beyond the waist-opening.

A liquid-absorbent structure 70 is provided on the body-facing side of the inner sheet 30. The liquid-absorbent structure 70 comprises a liquid-absorbent core 74 formed of fluff pulp and/or super-absorbent polymer particles wrapped with a liquid-dispersant sheet (unnumbered) and a cover sheet 75 with which the garment-facing side, i.e., the side facing the inner sheet 30, of the core 74 is covered. The liquid-absorbent core 74 is contoured by opposite side edges 71 extending in the longitudinal direction Y and front and rear ends 72, 73 extending in the transverse direction X. The cover sheet 75 extends in the transverse direction X beyond the opposite side edges 71 and is folded back along the opposite side edges 71 toward the body-facing side of the liquid-absorbent core 74 to form leak-barrier cuffs 76. In this way, cuff sleeves 78 containing therein cuff-biasing elastic members 79 are formed along the opposite side edges 77 of the cover sheet 75. In short, the elastic members 79 are provided along distal edge portions of the leak-barrier cuffs 76 to elasticize the distal edge portions. The cuff-biasing elastic members 79 are attached in a stretched state in the longitudinal direction Y to the respective cuff sleeves 78 so that, upon contraction thereof, the opposite side edges 77 are spaced upward from the inner sheet 30 toward the wearer's skin and thereby prevent body waste from leaking out.

In the front waist region 11, the liquid-absorbent structure 70 lies on the body-facing side of the front waist sheet 61 and has its front end 72 covered with the front sleeve 26. In the rear waist region 12, the liquid-absorbent structure 70 lies on the garment-facing side of the rear waist sheet 62, i.e., between the rear waist sheet 62 and the inner sheet 30 and has its rear end 73 covered with the rear waist sheet 62. By covering at least the front and rear ends 72, 73 of the liquid-absorbent structure 70 with the front and rear sleeves 26, 27, respectively, it is possible to prevent the core material from falling off from the front and rear ends 72, 73.

The opposite leg side edges 23a, 23b are curved inwardly toward the imaginary longitudinal center line P-P with a distance therebetween gradually reducing to a minimum on the imaginary transverse center line Q-Q. More specifically, these leg side edges 23a, 23b extend substantially in parallel to each other in the vicinity of the imaginary transverse center line Q-Q and, in the front and rear waist regions 11, 12, extend obliquely with respect to the imaginary longitudinal center line P-P. It is not essential that these parallel and oblique segments are distinguishable from each other and it is also possible to provide each of these leg side edges 23a, 23b with a different shape, for example they may each describe a continuous curve, such as a circular arc.

Along these leg side edges 23a, 23b, leg elastic members 53a, 53b, 54a, 54b extend while being sandwiched between the inner and outer sheets 30, 40. Specifically, the front leg elastic members 53a, 53b are sandwiched between the inner sheet 30 and the front outer sheet section 40a while the rear leg elastic members 54a, 54b are sandwiched between the inner sheet 30 and the rear outer sheet section 40b. The front and rear leg elastic members 53a, 53b, 54a, 54b are preferably formed of an elastic non-woven fabric but other elastic materials such as rubber strings also can be used. These front and rear leg elastic members 53a, 53b, 54a, 54b are bonded in a stretched state to the oblique segments of the leg side edges 23a, 23b, respectively, so as to be elastically contractible. If the leg side edges have a different shape to that exemplified here, the leg elastic members are bonded in a stretched state to at least a correspondingly-positioned portion of the leg side edges. These front and rear leg elastic members 53a, 53b, 54a, 54b are bonded to at least one of the inner and outer sheets 30, 40 by adhesive (not shown).

Each of the front and rear leg elastic members 53a, 53b, 54a, 54b is formed into a flat band or flat tape shape and preferably has a width dimension in a range of about 10 to 30 mm and preferably has a stretch ratio in a range of about 1.5 to 3.

In a preferred embodiment, the leg elastic members are formed of (1) an elastically stretchable non-woven fabric made of elastic fibers, such as urethane elastic fibers, or (2) an elastically stretchable non-woven fabric made of elastically stretchable fibers mixed with non-elastically stretchable thermoplastic synthetic fibers. In other embodiments, a plurality of rubber strings can be used as the leg elastic members.

While the front and rear leg elastic members 53a, 53b, 54a, 54b are spaced one from another in the vicinity of the imaginary transverse center line Q-Q in the particularly illustrated embodiment, in some further embodiments, it is possible to implement these elastic members in continuous fashion along the leg side edges. In such further embodiments, the outer sheet 40 may be implemented in the form of a continuous sheet, without being separated into the front and rear outer sheet sections 40a, 40b.

Referring to FIG. 5, the outer sheet 40 is formed on the garment-facing side thereof with a plurality of depressions 44. The depressions 44 are formed by heat and/or pressure treatment so as to be depressed or debossed from the garment-facing side of the outer sheet 40 toward the body-facing side thereof.

These depressions 44 are arranged intermittently along a plurality of rows and columns extending obliquely with respect to the imaginary center line P-P and intersecting the imaginary center line P-P. Specifically, the depressions 44 are arranged on a plurality of rows 45, 47 extending from the top left toward the bottom right, and on a plurality of columns 46, 48 extending from the top right toward the bottom left on the front and rear outer sheet sections 40a, 40b, respectively. The rows 45, 47 and the columns 46, 48 form a lattice pattern and, in the particularly illustrated embodiment, are substantially orthogonal one to another.

The angles at which the rows 45 and the columns 46 extend relative to the longitudinal direction Y on the front outer sheet section 40a are, in the particularly illustrated embodiment, set to coincide with the angles at which the oblique segments of the opposite leg side edges 23a, 23b extend relative to the longitudinal direction Y in the front waist region 11.

At least one of the rows 45 and at least one of the columns 46 extend along and overlap the front leg elastic members 53a, 53b, respectively. The angles at which the rows 47 and the columns 48 extend relative to the longitudinal direction Y on the rear outer sheet section 40a are, in the particularly illustrated embodiment, set to coincide with the angles at which the oblique segments of the opposite leg side edges 23a, 23b extend relative to the longitudinal direction Y in the rear waist region 12. At least one of the rows 47 and at least one of the columns 48 extend along and overlap the rear leg elastic members 54b, 54a, respectively.

The expression "extend along the leg side edges" used herein (including in the claims) should be understood to be inclusive of the cases in which the rows and columns conform in shape to the associated leg side edges 23a, 23b completely, substantially or partially. This expression therefore includes the groove extending along only a section of a leg side edge.

In the particularly illustrated embodiment, the angles at which the rows 45, 47 and the columns 46, 48 extend substantially coincides with the angles at which the oblique segments of the leg side edges 23a, 23b extend in the front and rear waist regions 11, 12. For the leg side edges 23a, 23b curved to describe circular arcs or another shape, the rows 45, 47 and the columns 46, 48 may be laid on the outer sheet 40 to substantially conform in shape with the leg side edges 23a, 23b.

Referring to FIGS. 6A and 6B, each of the depressions 44 in the exemplified embodiment is an about 0.7 mm by 0.7 mm square. In other embodiments, the depressions may take other shapes such as triangles, pentagons, hexagons or circles or similar irregular shapes: the shape of the depressions is not essential. A distance t1 between each pair of the adjacent depressions 44 in the rows 45, 47 as well as a distance t2 between each pair of the adjacent depressions 44 in the columns 46, 48 is about 0.8 mm. A distance t3 between each pair of the adjacent rows 45, 47 as well as a distance t4 between each pair of the adjacent columns 46, 48 is about 5.3 mm. While FIG. 6A shows only the front outer sheet section 40a, it is similarly applicable to the rear outer sheet section 40b.

Upon contraction of the front and rear leg elastic members 53a, 53b, 54a, 54b, the front and rear outer sheet sections 40a, 40b both formed with the depressions 44 also contract. As apparent from FIGS. 7A and 7B, contraction of the front leg elastic member 53a reduces the distance t1 between each pair of the adjacent depressions 44 in a series of depressions 44 formed on the row 45 extending along the leg side edge 23a of the front outer sheet section 40a.

In view of the fact that the depressions 44 are formed by locally fusing component fibers in the course of the heat treatment, the outer sheet 40 has relatively high stiffness and shape retention in the regions defined by the depressions 44. In contrast, the component fibers present between each pair of the adjacent depressions 44 are readily deformable so as to protrude toward the wearer's garment and, in consequence, the distance t1 between each pair of the adjacent depressions is narrowed until each pair of the adjacent depressions 44 in the row 45 are made closely contiguous to each other. The distance t4 is also narrowed as the distance t1 is narrowed.

Indeed, as shown in FIGS. 7A and 7B, the distance t1 between each pair of the adjacent depressions 44 of the row or column (e.g., row 45) that overlaps one of the leg elastic members 53a, 53b, 54a, 54b, upon contraction of the respective leg elastic member (e.g., 53a), becomes narrower than the dimension of each depression 44 as measure along the respective leg elastic member (e.g., 53a). Such a series of depressions 44 on a row or column (e.g., row 45) with the narrowed distance t1 between each pair of the adjacent depressions extends along the respective leg elastic member (e.g., 53a).

In the front leg elastic member 53b, a series of depressions 44 arranged in the column 46 contract to narrow the distance t2 and, in consequence, to be closely contiguous to each other. In the similar fashion, the column 48 contracts together with the rear leg elastic member 54a while a series of depressions 44 on the row 47 contracts together with the rear leg elastic member 54b to narrow the distance t2 and the distance t1 between each pair of the adjacent depressions 44 and thereby to be closely contiguous to each other, respectively.

A series of depressions 44 on the row or column (e.g., row 45) with the narrowed distance t1 between each pair of the adjacent depressions, due to the contraction of the respective leg elastic member (e.g., 53a), defines a folding guide line about which the outer sheet 40, the inner sheet 30 and the respective leg elastic member (e.g., 53a) are foldable to thereby conform in shape to the wearer's body when the diaper is being worn.

In other words, after the series of depressions closely contiguous together have been formed as a folding line in a manner as described above, the outer sheet 40 can be easily folded along these folding lines and, following this, the front and rear leg elastic members 53a, 53b, 54a, 54b and the inner sheet 30 bonded to the outer sheet 40 can be also easily folded. More specifically, the inner and outer sheets 30, 40 and the front and rear leg elastic members 53a, 53b, 54a, 54b are easily folded around the leg-openings in the vicinity of the wearer's thighs including inguinal regions. In this way, these sheets and members can be deformed in conformity to the vicinity of the wearer's thigh and put in close contact with the wearer's thighs and thereby to prevent body waste from leaking out between the thighs and the respective leg-openings. In addition, the front and rear leg elastic members 53a, 53b, 54a, 54b are deformable depending on the individual wearer's body to protect the wearer from skin trouble and, at the same time, to improve wearing comfort.

EXAMPLE

On the outer sheet 40 made of a crimped spun bonded fibrous non-wove fabric having a basis weight of about 30 g/m², bending stiffness and hysteresis were measured. To this outer sheet 40, the front leg elastic members 53a, 53b or the rear leg elastic members 54a, 54b formed of an elastic fibrous non-woven fabric were attached at a stretch ratio of about 2.2. Bending stiffness and hysteresis were measured on the outer sheet 40 folded along one of the rows 45 or one of the columns 46. For measurement of the bending stiffness and the hysteresis, Automatic Pure Bending Tester KES-FB2-AUTO-A (KATO TECH CO., LTD.) was used. The crimped spun bonded fibrous non-woven fabric (i.e., the outer sheet 40) was bonded to the elastic fibrous non-woven fabric (i.e., the leg elastic members) and 20 cm×20 cm test pieces were cut from this laminate. Respective measurements were conducted at a bending deformation rate of 0.5 cm$^{-1}$/sec.

As the result of these measurements, the bending stiffness was $0.1053 \times 10^{-4}$ Nm/m and the hysteresis was $0.0485 \times 10^{-2}$ N/m.

Similar measurements of the bending stiffness and the hysteresis were conducted on the outer sheet 40 made of a non-crimped spun bonded fibrous non-woven fabric having a basis weight of about 25 g/m². This outer sheet 40 was formed with the depressions 44 each defined by an about 0.4 mm by 0.4 mm square and arranged in a pattern of a hound's tooth check wherein a distance between each pair of the adjacent depressions 44 was about 1.7 mm. As a result of the measurements, the bending stiffness was $0.1480 \times 10^{-4}$ Nm/m and the hysteresis was $0.1100 \times 10^{-2}$ N/m.

The result of these measurements suggests that the crimped fibrous non-woven fabric may be used as the outer sheet 40 and the depressions 44 may be arranged to define the rows 45, 47 and the columns 46, 48 to reduce the bending stiffness as well as the hysteresis and thereby to soften the article.

Specifically, the use of a crimped fibrous non-woven fabric as the outer sheet 40 causes component fibers between each pair of the adjacent depressions 44 to protrude toward the wearer's garment and thereby to increase bulk of the outer sheet 40 in the thickness direction and to improve a cushioning characteristics. As a consequence, texture is improved and the article can be more comfortable for the wearer. The crimped fibers may be obtained by the technique widely used in the relevant technical field, for example, mechanical or heat treatment.

While the depressions 44 are formed over the entire areas of the front and rear outer sheet sections 40a, 40b in the particularly illustrated embodiment, in some embodiments, it is sufficient to form a series of depressions 44 in at least one of the front and rear outer sheet sections 40a, 40b along the respective leg side edges thereof to achieve the desired effect. However, when the outer sheet 40 is fully formed with the depressions 44, it is possible to assure that not only the deformability along the leg side edges 23a, 23b but also the texture over the entire area of the outer sheet 40 is improved. These depressions 44 may be used to provide the diaper 10 with a desired pattern and make the diaper decorative.

While the depressions 44 are arranged to define the rows 45, 47 and the columns 46, 48 in the particularly illustrated embodiment, the invention is not limited to such arrangement. For example, the depressions 44 may be distributed in so-called a hound's tooth check pattern to ensure each pair of the depressions 44 adjacent in the longitudinal direction Y as well as in the transverse direction X to be spaced from each other. Alternatively, the depressions 44 may be arranged on a line along each of the leg side edges 23a, 23b. Any pattern can be implemented so long as a series of depressions closely contiguous to each other can be formed along each of the leg side edges 23a, 23b. With the outer sheet 40 formed with the rows 45, 47 and the columns 46, 48 of the depressions 44, the fabric become bulky between these rows and columns as the diaper 10 contracts in the longitudinal direction Y and the transverse direction X under the contraction of the elastic members. Such bulkiness provides the diaper 10 with an appearance and a touch just like a quilt.

While the depressions 44 are intermittently arranged in rows and columns so that the depressions 44 may be closely contiguous to each other as the front and rear leg elastic members 53a, 53b, 54a, 54b contract according to the particularly illustrated embodiment, the invention is not limited to this arrangement. It is also possible without departing from the scope of the invention that the depressions define the continuous grooves without any interruption such as distance t1 shown in FIGS. 6A and 7A. Shape, distance and placement of the depressions 44 also are not limited to the particularly illustrated embodiment and may be appropriately varied.

While the depressions 44 are formed by heat and pressure treatment in the particularly illustrated embodiment, it is also possible to form the depressions 44, for example, by press working without heating.

While the depressions 44 are formed as squares in the particularly illustrated embodiment, it is also possible to form the depressions 44 in any shapes, including but not limited to, round, triangular, rectangular, diamond, oval shapes etc. The depressions 44 in a single diaper can also be formed of multiple shapes.

While the front and rear leg elastic members 53a, 53b, 54a, 54b are attached to the chassis so as to be sandwiched between the inner and outer sheets 30, 40 in the particularly illustrated embodiment, it is possible to attach these elastic members to the side of the inner sheet 30 closer to the wearer's skin or the side of the outer sheet 40 closer to the wearer's garment.

In the particularly illustrated embodiment, the front and rear leg elastic members 53a, 53b, 54a, 54b are attached to the front and rear waist regions 11, 12 along the leg side edges 23a, 23b. Alternatively, it is also possible without departing from the scope of the invention to attach these leg elastic members to at least one of the front and rear waist regions 11, 12 so far as these leg side edges 23a, 23b can be elasticized, in other words, so far as the front and rear leg elastic members 53a, 53b, 54a, 54b can contract along the leg side edges 23a, 23b.

FIG. 8 is a view similar to FIG. 6A, illustrating another depression pattern in accordance with one or more further embodiments. In FIG. 8, one or more of the rows 45, 47 and the columns 46, 48 overlap the front and rear leg elastic members 53a, 54b, 53b, 54a. Specifically, two of the rows 45 overlap the leg elastic member 53a. Two or more of the rows or columns overlapping the leg elastic member in this manner further facilitate the front and rear leg elastic members 53a, 53b, 54a, 54b as well as the inner and outer sheets 30, 40 to be folded and reliably put the diaper in close contact with the wearer's skin. Two or more of the rows 45, 47 and the columns 46, 48 may be arranged to overlap the front and rear leg elastic members 53a, 54b, 53b, 54a to ensure that the leg side edges 23a, 23b can be folded in a stepwise fashion so as to come in close contact with the wearer's skin over a large range and thereby to restrict the leg side edges from irritating the wearer's skin locally.

In FIG. 8, while each two of the rows 45, 47 and the columns 46, 48 overlap the front and rear leg elastic members 53a, 54b, 53b, 54a, respectively, the invention is not limited to such arrangement and it is possible to lay on three or more of these rows and columns so as to overlap these elastic members. In this case, the distance t3 between each pair of the adjacent rows, the distance t4 between each pair of the adjacent columns may be narrowed, the distance t1, t2 between each pair of the adjacent depressions 44 may be narrowed or the width dimensions of the front and rear leg elastic members 53a, 53b, 54a, 54b may be enlarged.

The aspects of the present invention described above may be arranged in at least following items:

(i) The wearing article (10) comprising a chassis (20) including a longitudinal direction (Y), a transverse direction (X), a body-facing side, a garment-facing side opposite to the body-facing side, a front waist region (11), a rear waist region (12), a crotch region (13) extending between the front and rear waist regions and leg side edges (23a, 23b), leg elastic members (53a, 53b, 54a, 54b) of an elastic fibrous non-woven fabric formed into a flat band shape and attached to the chassis along the leg side edges, and the chassis having regions each of which overlaps one of the leg elastic members and comprises at least one series of depressions (44) extending along the respective leg side edge.

The aspect of the present invention described in the above item (i) may provide one or more of the following advantageous effects:

(a) In the regions of the chassis overlapping the leg elastic members, the chassis is formed with series of depressions along the leg side edges. This unique arrangement facilitates the chassis and the leg elastic members to be folded along these series of depressions and thereby to be deformed along the wearer's thighs including the inguinal regions. Consequentially, the chassis is reliably put in close contact with the wearer's skin to prevent leak of body waste and, at the same time, to restrict any skin trouble due to irritation by the chassis and the leg elastic members.

Additionally, one or more of the following embodiments are provided in accordance with further aspects:

(ii) The at least one series of depressions comprises (e.g. one of the rows or columns mentioned in the exemplified embodiments) a plurality of depressions (44) arranged intermittently in at least one row along the respective leg side edge.

(iii) The chassis comprises an inner sheet (30) lying on the body-facing side and an outer sheet (40) lying on the garment-facing side, the leg elastic members are attached to the chassis so as to be sandwiched between the inner and outer sheets, and the depressions are formed in the body-facing side of the outer sheet.

(iv) The outer sheet is formed of a fibrous non-woven fabric of crimped fibers.

(v) Each of the leg elastic members has a width dimension in a range of about 10 to 30 mm.

(vi) Each of the leg elastic members has a stretch ration in a range of about 1.5 to 3.

(vii) The outer sheet comprises a front outer sheet section (40a) lying on the front waist region and a rear outer sheet (40b) section lying on the rear waist region. The front and rear outer sheet sections are spaced from each other in the longitudinal direction in a vicinity of an imaginary transverse center line (Q-Q) of the chassis. The chassis comprises a lattice pattern of the depressions arranged in a plurality of rows (45, 47) and columns (46, 48) over substantially entire areas of the front and rear outer sheet sections. The at least one series of depressions (44) is defined by at least one of the rows or columns that overlaps the respective leg elastic member.

(viii) The wearing article further comprises in at least one of the front and rear waist regions, an elasticized front or rear waist sheet (61, 62).

(ix) The wearing article further comprises a liquid-absorbent structure (70) disposed on the body-facing side of the chassis.

(x) The liquid-absorbent structure further has a cover sheet (75) on the inner sheet of the chassis. The cover sheet covers a garment-facing side of the liquid-absorbent structure, extends in the transverse direction beyond opposite side edges (71) of the liquid-absorbent structure and is folded back along the side edges toward the liquid-absorbent structure to form leak-barrier cuffs (76) wherein at least distal edge portions of the leak-barrier cuffs are elasticized.

According to the embodiments in the above (ii) to (x), the advantageous effect(s) set forth at (a) is/are better ensured. Further advantageous effects of the respective embodiments may be obtained as discussed in the respective related descriptions.

The aspects of the present invention described above may be further arranged in at least the following further items:

(xi) The wearing article (10) comprising a chassis (20) including a longitudinal direction (Y), a transverse direction (X), a body-facing side, a garment-facing side opposite to the body-facing side, a front waist region (11), a rear waist region (12), a crotch region (13) extending between the front and rear waist regions and leg side edges (23a, 23b), leg elastic members (53a, 53b, 54a, 54b) of a flat band shape and being attached to the chassis along the leg side edges, and the chassis having, along at least one of the leg elastic members, at least one folding guide line about which the chassis and the respective leg elastic member are foldable to thereby conform in shape to a wearer's body when the diaper is being worn by the wearer.

The aspect of the present invention described in the above item (xi) may provide one or more of the advantageous effect (s) as discussed at item (a).

Additionally, one or more of the following embodiments are provided in accordance with further aspects:

(xii) The at least one folding guide line comprises a series of depressions (44) arranged intermittently in at least one row that overlaps and extends along the respective leg elastic member.

(xiii) The chassis comprises an inner sheet (30) lying on the body-facing side and an outer sheet (40) lying on the garment-facing side;

the leg elastic members are attached to the chassis so as to be sandwiched between the inner and outer sheets; and the depressions extend from the garment-facing side toward the body-facing side of the outer sheet.

(xiv) The outer sheet is formed of a fibrous non-woven fabric of crimped fibers.

(xv) Each of the leg elastic members has a width dimension in a range of about 10 to 30 mm.

(xvi) Each of the leg elastic members has a stretch ratio in a range of about 1.5 to 3.

(xvii) The chassis comprises a lattice pattern of the depressions arranged in a plurality of rows (45, 47) and columns (46, 48) over at least one of the front and rear waist regions.

The at least one folding guide line is defined by at least one of the rows or columns that overlaps the respective leg elastic member.

(xviii) The depressions comprise fused fibers of the outer sheet.

(xix) The depressions comprise compressed fibers of the outer sheet.

(xx) A distance (t1, FIG. 7A) between each pair of the adjacent depressions is smaller than a dimension of each the depression as measured along the respective leg elastic member, whereby the series of depressions is closely contiguous to each other defines the folding guide line. According to the embodiments in the above (xii) to (xx), the advantageous effect(s) set forth at (a) is/are better ensured. Further advantageous effects of the respective embodiments may be obtained as discussed in the respective related descriptions.

The invention claimed is:

1. A wearing article, comprising:
a chassis including a longitudinal direction, a transverse direction, a body-facing side, a garment-facing side opposite to said body-facing side, a front waist region, a rear waist region, a crotch region extending between said front and rear waist regions, and leg side edges; and
leg elastic members of a flat band shape and being attached to said chassis along said leg side edges,
wherein
said chassis has, along at least one of said leg elastic members, at least one folding guide line about which the chassis and the respective leg elastic member are foldable to thereby conform in shape to a wearer's body when the diaper is being worn by the wearer, and
said at least one folding guide line comprises a series of depressions arranged intermittently in at least one row that overlaps and extends along said respective leg elastic member.

2. The wearing article defined by claim 1, wherein:
said chassis comprises an inner sheet lying on said body-facing side and an outer sheet lying on said garment-facing side;
said leg elastic members are attached to the chassis so as to be sandwiched between said inner and outer sheets; and
said depressions extend from the garment-facing side toward the body-facing side of said outer sheet.

3. The wearing article defined by claim 2, wherein said outer sheet is formed of a fibrous non-woven fabric of crimped fibers.

4. The wearing article defined by claim 2, wherein
said chassis comprises a lattice pattern of the depressions arranged in a plurality of rows and columns over at least one of said front and rear waist regions; and
said at least one folding guide line is defined by at least one of said rows or columns that overlaps the respective leg elastic member.

5. The wearing article defined by claim 2, wherein the depressions comprise fused fibers of said outer sheet.

6. The wearing article defined by claim 2, wherein the depressions comprise compressed fibers of said outer sheet.

7. The wearing article defined by claim 1, wherein each of said leg elastic members has a width dimension in a range of about 10 to 30 mm.

8. The wearing article defined by claim 1, wherein each of said leg elastic members has a stretch ratio in a range of about 1.5 to 3.

9. The wearing article defined by claim 1, wherein a distance between each pair of the adjacent depressions is smaller than a dimension of each said depression as measured along the respective leg elastic member, whereby said series of depressions is closely contiguous to each other and defines said folding guide line.

* * * * *